(12) United States Patent
Griffin et al.

(10) Patent No.: US 9,561,099 B1
(45) Date of Patent: Feb. 7, 2017

(54) ELECTROLARYNX CONTROL BUTTON ARRANGEMENT

(71) Applicants: Clifford Jay Griffin, Murrieta, CA (US); Mark Andrew Robertson, Murrieta, CA (US)

(72) Inventors: Clifford Jay Griffin, Murrieta, CA (US); Mark Andrew Robertson, Murrieta, CA (US)

(73) Assignee: Griffin Laboratories, Temecula, CA (US)

( * ) Notice: Subject to any disclaimer, the term of this patent is extended or adjusted under 35 U.S.C. 154(b) by 0 days.

(21) Appl. No.: 15/043,516

(22) Filed: Feb. 13, 2016

Related U.S. Application Data

(60) Provisional application No. 62/273,319, filed on Dec. 30, 2015.

(51) Int. Cl.
| | | |
|---|---|---|
| *H03G 3/00* | (2006.01) | |
| *A61F 2/20* | (2006.01) | |
| *H03G 5/10* | (2006.01) | |
| *H03G 3/18* | (2006.01) | |
| *H03G 9/14* | (2006.01) | |
| *A61F 2/48* | (2006.01) | |

(52) U.S. Cl.
CPC ...... *A61F 2/20* (2013.01); *H03G 3/18* (2013.01); *H03G 5/10* (2013.01); *H03G 9/14* (2013.01); *A61F 2002/206* (2013.01); *A61F 2002/481* (2013.01)

(58) Field of Classification Search
CPC .............................. A61F 2/20; A61F 2002/206
USPC .................................... 381/70, 109, 103
See application file for complete search history.

(56) References Cited

U.S. PATENT DOCUMENTS

| | | | | |
|---|---|---|---|---|
| 4,685,448 A | * | 8/1987 | Shames | A61F 5/58 128/905 |
| 4,691,360 A | * | 9/1987 | Bloomfield, III | A63H 5/00 381/70 |
| 5,812,681 A | | 9/1998 | Griffin | |
| 6,252,966 B1 | | 6/2001 | Griffin | |
| 9,031,249 B1 | | 5/2015 | Griffin | |
| 9,116,539 B1 | | 8/2015 | Griffin | |
| 2003/0031326 A1 | * | 2/2003 | Lukacovic | A61F 2/20 381/70 |

(Continued)

*Primary Examiner* — Disler Paul
(74) *Attorney, Agent, or Firm* — Loyal McKinley Hanson

(57) ABSTRACT

An electrolarynx includes tone-producing circuitry, a power switch to turn on the circuitry, a control button (i.e., a pushbutton) to actuate the power switch, a pressure-sensitive-resistor (PSR) that is physically coupled to the pushbutton, and a mode switch. PSR resistance is dependent on the amount of pressure applied to the pushbutton, and the tone-producing circuitry is configured to respond to such variations in PSR resistance according to a user-selected mode of electrolarynx operation set by operation of the mode switch. Said modes preferably include multiple frequency-varying modes (FVMs) in which the frequency of the electrolarynx tone is varied with different sensitivities to variations in PSR resistance, and multiple volume-varying modes (VVMs) having different sensitivities. A preferred embodiment also includes a communications-link mode, for receiving control information from an external device, and a disabled mode. Preferably, the tone-producing circuitry includes a microcontroller component that is configured for electrolarynx operation under program control.

7 Claims, 5 Drawing Sheets

(56) References Cited

U.S. PATENT DOCUMENTS

2009/0174823 A1* 7/2009 Knutson ................. H04S 7/307
348/738

* cited by examiner

ELECTROLARYNX CONTROL BUTTON ARRANGEMENT

CROSS REFERENCE TO RELATED APPLICATION

This application claims the benefit of U.S. Provisional Patent Application Ser. No. 62/273,319 filed Dec. 30, 2015.

BACKGROUND OF THE INVENTION

1. Technical Field

This invention relates generally to the electromechanical speech aids commonly referred to as artificial larynxes and as electrolarynxes, and more particularly to an improved electrolarynx construction with increased functionality.

2. Description of Related Art

A person without normal use of their vocal cords or larynx often uses an electrolarynx to speak. The electrolarynx includes a sound-producing component that delivers an electrolarynx tone (e.g., a buzzing sound) having a fundamental frequency in the speech range of the average human voice. To speak, the user introduces this artificially generated tone into a resonant speech cavity (i.e., the mouth, nose, or pharynx). While doing so, the user modulates the electrolarynx tone by varying the shape of the resonant speech cavity and by making the usual tongue, teeth, and lip constrictions so as to articulate the modulated tone as human speech.

U.S. Pat. Nos. 5,812,681; 6,252,966; 9,031,249; and U.S. Pat. No. 9,116,539 issued to Clifford J. Griffin describe some existing electrolarynxes. Each of those electrolarynxes typically includes a four-inch to five-inch long case that houses an electronic circuit board, a battery, an electro-mechanical transducer for producing vibrations (i.e., the electrolarynx tone), a volume control, and a power switch. The user grasps the case in one hand, actuates the power switch and volume control, and then presses the transducer portion of the electrolarynx against the outside of their throat so that electrolarynx tone vibrations travel through the throat tissues and into the mouth and throat for modulation and articulation.

One such electrolarynx includes a pressure-sensitive resistor (PSR) coupled to a pushbutton; the user depresses the pushbutton with their thumb to actuate the power switch while varying the pressure on the PSR. The PSR is connected to electronic circuitry that varies the frequency of the electrolarynx tone according to changes in the amount of pressure applied to the PSR. That way, the pushbutton-PSR combination enables both electrolarynx power-on and frequency variation of the electrolarynx tone with minimal, unnoticeable movement of the user pressing the pushbutton. Operation is easy, and a wide and continuous range of frequencies allows for increased control and subtle voice inflection, including syllable-specific intonation which may be used to approximate regionally specific or country specific voice patterns. Nevertheless, variation of electrolarynx volume is not as easy.

SUMMARY OF THE INVENTION

In view of the foregoing, it is a primary objective of the present invention to provide an electrolarynx having significant improvements and increase functionality, including ease of both frequency and volume variation. The present invention achieves this objective by providing an electrolarynx with a pushbutton-PSR combination along with means for enabling a user to select which electrolarynx tone attribute is affected by variations in the resistance of the PSR. The user simply operates a mode switch on the electrolarynx to select a desired one of multiple modes of electrolarynx operation.

To paraphrase some of the more precise language appearing in the claims and further introduce the nomenclature used, an electrolarynx constructed according to the invention includes an enhanced, multimode pushbutton-PSR arrangement. The electrolarynx includes (i) a case, (ii) tone-producing circuitry on the case for producing an electrolarynx tone having a frequency and a volume, (iii) a power switch on the case for turning on power to the tone-producing circuitry, (iv) a pushbutton on the case that is operatively connected to the power switch for purposes of enabling a user to activate the power switch, and (v) a PSR physically coupled to the pushbutton so that the PSR resistor has a resistance value dependent on the pressure a user applies to the pushbutton.

According to a major aspect of the invention, the tone-producing circuitry is configured to operate in multiple user-selected modes of electrolarynx operation. In a first frequency-varying mode (i.e., a first FVM), the tone-producing circuitry varies the frequency of the electrolarynx tone according to variations in the PSR resistance value. In a first volume-varying mode (i.e., a first VVM), the tone-producing circuitry varies the volume. A mode switch component of the electrolarynx enables the user to set a user-selected mode of operation. Preferably, additional modes of operation are included, some of which vary sensitivity to changes in the PSR resistance value.

Thus, the invention provides an electrolarynx having significant improvements and increase functionality, including ease of both frequency and volume variation using a single pushbutton-PSR combination. The following illustrative drawings and detailed description make the foregoing and other objectives, features, and advantages of the invention more apparent.

DESCRIPTION OF THE PREFERRED EMBODIMENTS

Figure 1:
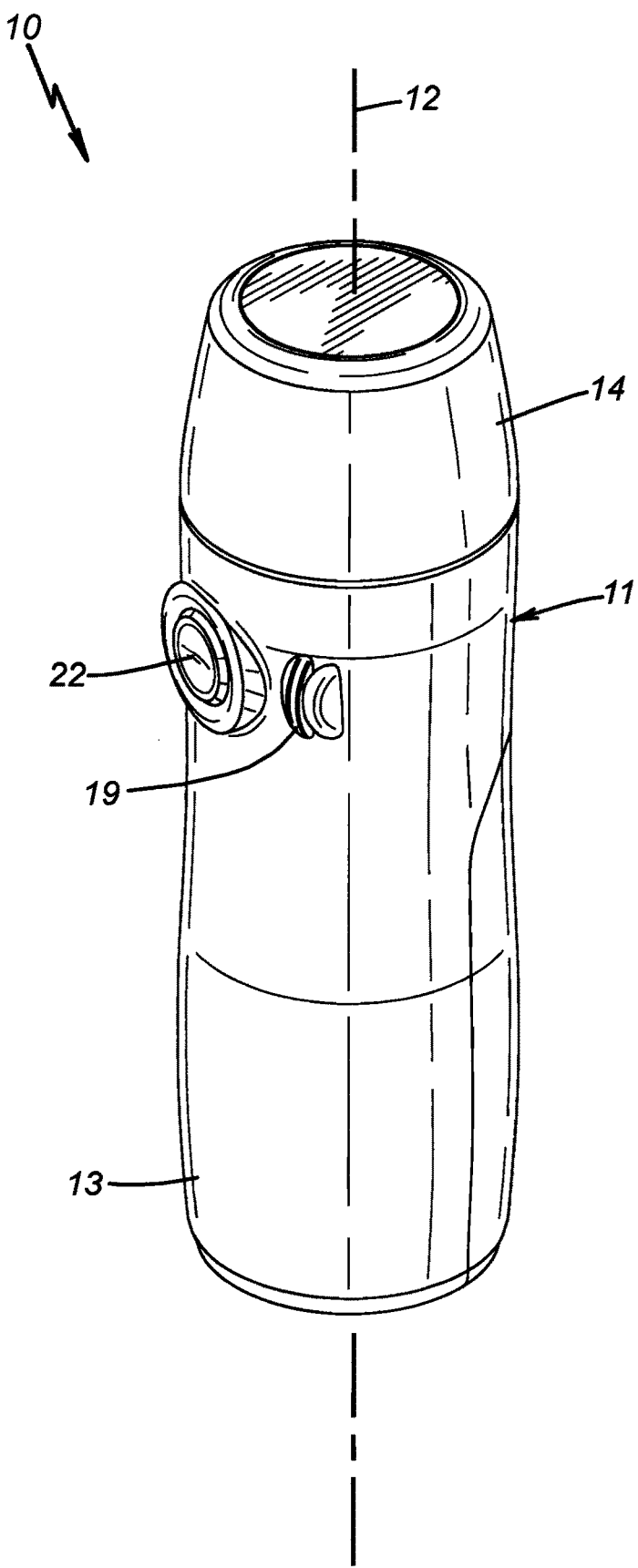
FIG. 1 of the drawings is a first perspective view of an electrolarynx constructed according to the invention, showing the distal or forward end portion of the electrolarynx positioned toward the top of the drawing sheet, a pushbutton (i.e., a control-button) side portion positioned toward the left side of the drawing sheet, and a proximal (i.e., a bottom portion) positioned toward the bottom of the drawing sheet.
Figure 2:
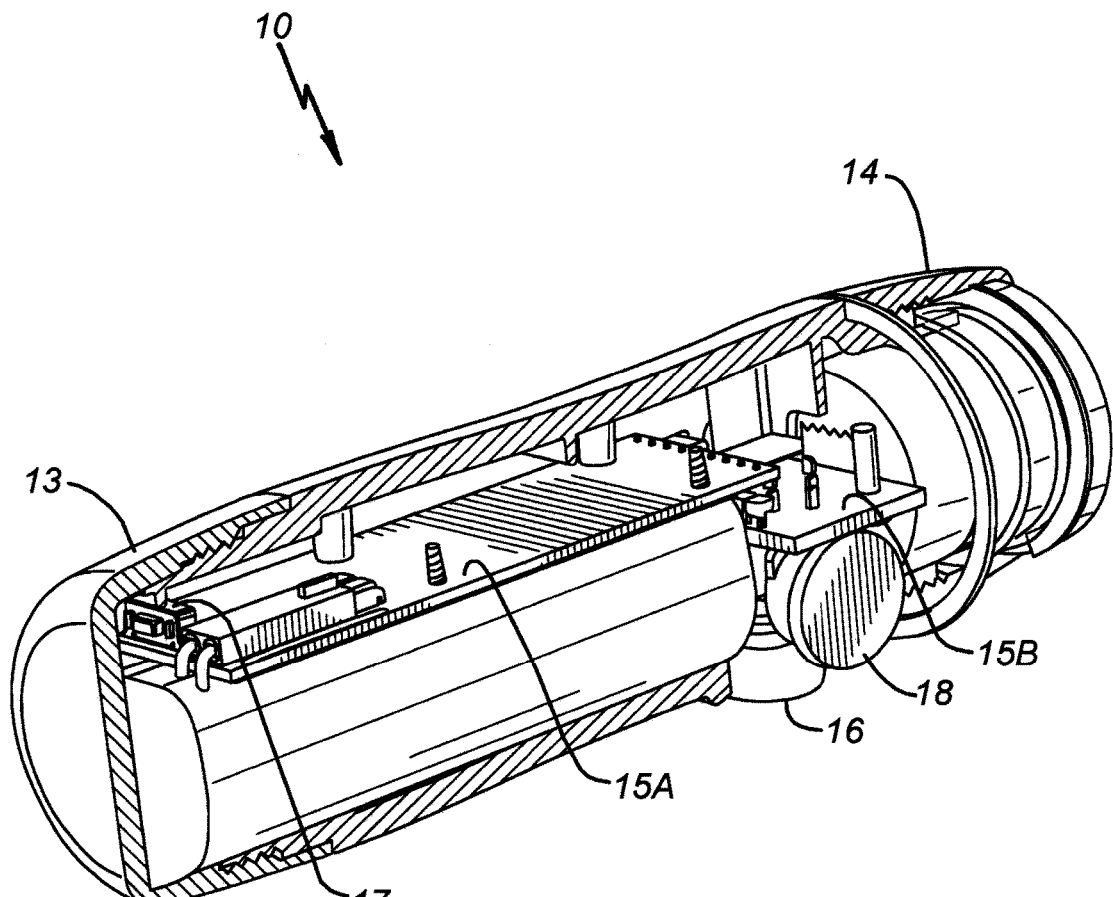
FIG. 2 of the drawings is a second perspective view of the electrolarynx, showing the distal end portion positioned toward the right side of the drawing sheet, the pushbutton side portion positioned toward the bottom of the drawing sheet, and the proximal end portion positioned toward the right side of the drawing sheet.
Figure 3:
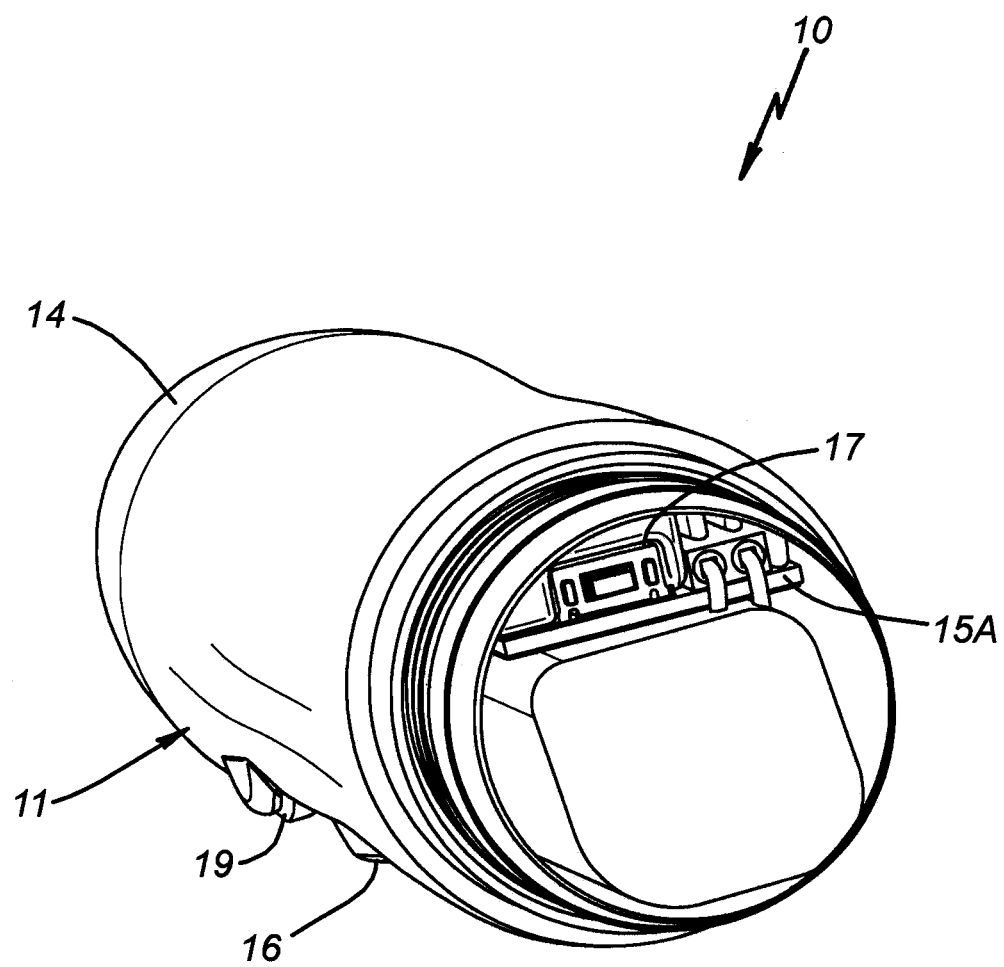
FIG. 3 of the drawings is a third perspective view of the electrolarynx, with the bottom end cap removed so that the mode switch is visible, as viewed facing toward the proximal end portion of the electrolarynx.

FIGS. 1, 2, and 3 of the drawings shows an electrolarynx 10 constructed according to the present invention. The electrolarynx 10 may be similar in many respects to the electrolarynxes described in U.S. Pat. Nos. 5,812,681; 6,252,966; 9,031,249; and 9,116,539. Those patents are incorporated herein in their entireties by this reference for all the information they provide.

Generally, the electrolarynx 10 includes a case 11 (FIGS. 1, 2, and 3) that extends along a central axis of elongation 12 of the case 11, between a first or bottom end cap 13 at a proximal or bottom end portion of the case (FIGS. 1 and 2) and a second or top end cap at a distal or forward end portion of the case (FIGS. 1 and 2). The user grasps the case 11, presses the top end cap 14 (i.e., the sound-producing transducer portion at the forward end of the electrolarynx 10) against the outside of their throat in order to introduce an electrolarynx tone to their mouth and throat, and then modulates that tone by holding their breath while varying the shape of the resonant speech cavity and making the usual tongue, teeth, and lip constrictions so as to articulate the modulated tone as human speech.

The case 11 is a handheld component (e.g., a molded-plastic or metal alloy component) having an overall length of about four to five inches measured along the central axis of elongation 12. Of course, that dimension provides an idea of the size of the various components of the illustrated embodiment; it is not critical to the present invention. The case 11 includes a first longitudinally extending section (i.e., a first half) and a second longitudinally extending section (i.e., a second half) that, when fully assembled, are held together by the bottom and top end caps 13 and 14. The assembler person screws the bottom and top end caps 13 and 14 onto the first and second sections, in threaded engagement of the first and second sections, to hold the two halves together.

Figure 4:
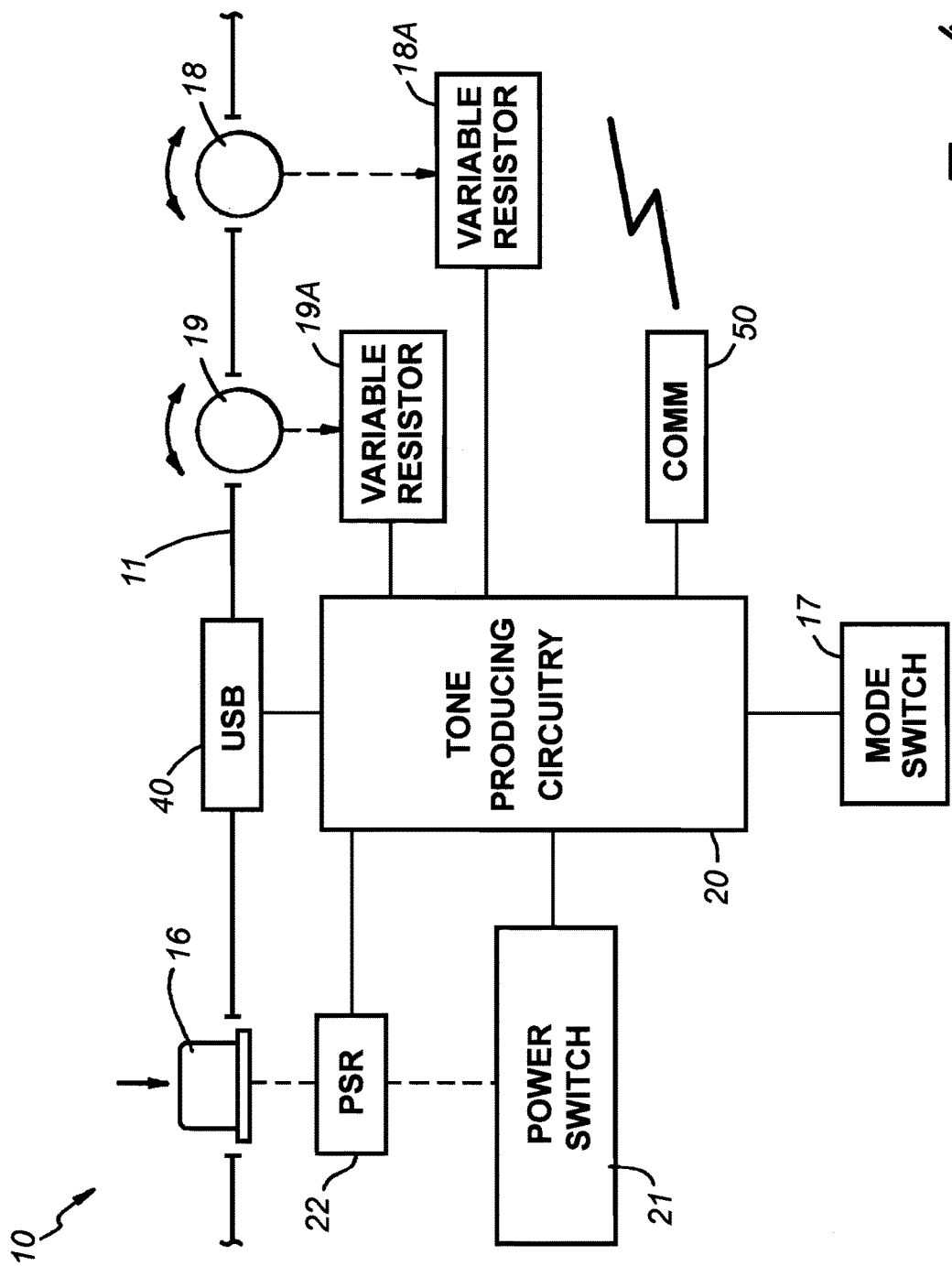
FIG. 4 is a diagrammatic block diagram of the electrolarynx tone-producing circuitry, including the pushbutton, the PSR, and the mode switch.

With the first and second sections fully assembled, the case 11 defines a hollow interior that provides a space for a battery-powered circuit board 15 that is the combination of a first circuit board section 15A and a second circuit board section 15B (FIG. 2). Circuitry on and/or connected to the circuit board 15 includes a switch-activating pushbutton 16 (i.e., a switch-depressing component) that is identified in FIGS. 1 through 5, a mode switch 17 (FIGS. 2 through 5), a frequency-controlling first thumbwheel 18 (FIGS. 2 and 4), and a volume-controlling thumbwheel 19 (FIGS. 1, 3, and 4). The user depresses the pushbutton 16 to turn on power to the electrolarynx 10 so that it produces an electrolarynx tone, while the user operates the thumbwheels 18 and 19 to set a desired frequency and volume of that tone.

FIG. 4 shows the components mentioned above, together with additional components of the electrolarynx 10 that are connected to electronic circuitry identified as "tone-producing circuitry 20." The tone-producing circuitry 20 includes a transducer component for producing the electrolarynx tone. It may take the form of a known type of electromechanical transducer assembly that includes a coil of magnet wire for producing a magnetic field such that it causes a plunger to vibrate against a button-like diaphragm and thereby produce a buzzing electrolarynx sound (i.e., the electrolarynx tone) having an audible fundamental frequency in the speech range of the average human voice (e.g., about 40 Hertz up to about 200 Hertz). Use of a linear motor falls within the broader inventive concepts and the term transducer component herein includes that alternative.

The frequency-controlling first thumbwheel 18 is connected to a first variable resistor 18A that is, in turn, connected to the tone-producing circuitry 20. Similarly, the volume-controlling second thumbwheel 19 is connected to a second variable resistor 19A that is connected to the tone-producing circuitry 20. In operation, the action of the user depressing the pushbutton 16 (e.g., a 0.4-inch diameter pushbutton) activates the switch 21 (i.e., turns on power) with the result that the tone-producing circuitry 20 produces the electrolarynx tone with a thumbwheel-determined value of frequency (TWDF) and thumbwheel-determined level of volume (TWDV) that are determined by the positions of the first and second thumbwheels 18 and 19.

According to a major aspect of the invention, the tone-producing circuitry 20 is configured to operate in multiple modes of electrolarynx operation. In a first frequency-varying mode (i.e., the first FVM), the tone-producing circuitry 20 enables the user to vary the frequency of the electrolarynx tone from the TWDF by varying pressure on the pushbutton 16 (e.g., similar to the technique described in U.S. Pat. No. 5,812,681). In the first volume-varying mode (i.e., the first VVM), the tone-producing circuitry 20 enables the user to vary the volume of the electrolarynx volume from the TWDV by varying pressure on the pushbutton 16. The user can preselect the first FVM or the first VVM using the mode switch 17 component of the electrolarynx circuitry.

More specifically, the electrolarynx 10 includes a pressure-sensitive resistor (i.e., a PSR 22 in FIG. 4) that is physically coupled to the pushbutton 16 (e.g., interposed between the pushbutton 16 and the switch 21) so that the pressure-sensitive resistor has a resistance value dependent on pressure applied by the user to the pushbutton 16. The illustrated pushbutton 16 extends from a user-accessible position on the exterior of the case 11, through the case 11 to the interior of the case 11, where it is mechanically coupled via the PSR 22 to the switch 21. The PSR 22 is a known type of component having a resistance value that varies according to the pressure applied to it; it is commercially available from various sources, including Interlink Electronics, Inc. of Camarillo, Calif. Depressing the pushbutton 16 results in pressure against the PSR 22 that varies its resistance. Thus, the user can depress the pushbutton 16 to turn on the electrolarynx tone, and also to vary the resistance of the PSR 22. The tone-producing circuitry 20 responds to variations in the resistance of the PSR 22 by varying the frequency or volume of the electrolarynx tone according to the selected mode of electrolarnyx operation.

Preferably, additional modes are provided for also, including, for example, a communications-link mode for enabling control from an external device, and a disabled mode for disabling response of the tone-producing circuitry 20 to the PSR 22. Moreover, five or more modes may be included. At initial power up of the electrolarynx 10 (e.g., by inserting a nine-volt battery), the tone-producing circuitry 20 preferably defaults to the disabled mode mentioned above. Preferably, a mode selected after initial power up is maintained in memory during periods that the electrolarynx 10 is not in use.

The mode switch 17 of the electrolarynx 10 enables a user to select a desired one of multiple modes of operation. The illustrated mode switch 17 is a momentary, normally open, pushbutton switch that the user operates for that purpose, with the tone-producing circuitry 20 responding to each operation of the mode switch 17 by stepping through multiple modes of operation. Other types of user input devices may be used for mode control instead within the broader inventive concepts of the present invention. For the illustrated mode switch 17, the user depresses it one time to select the first FVM and multiple times to select the first VVM.

Figure 5:
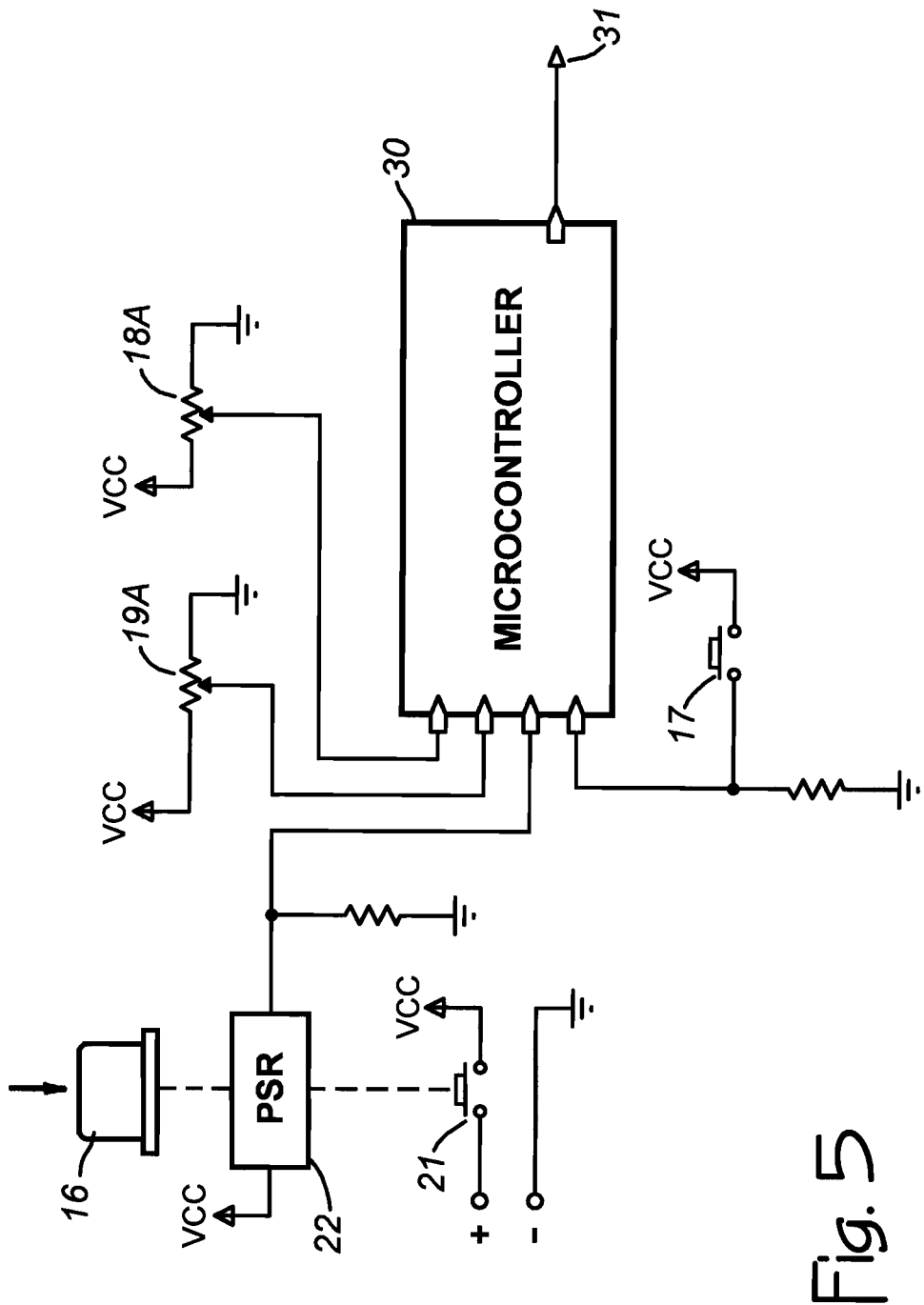
FIG. 5 is a schematic diagram showing connections to a microcontroller component of the tone-producing circuitry.

The tone-producing circuitry 20 in FIG. 4 is configured so that the electrolarynx 10 operates as herein described. In other words, it includes a combination of analog and/or digital circuit components that are interconnected (and programmed where required) to work together and function as stated. FIG. 5 shows the tone-producing circuitry 20 implemented with a microcontroller 30 that controls operation under program control to provide a transducer component drive signal at a line 31 in FIG. 5 that results in the electrolarynx tone. The illustrated microcontroller 30 is, for example, the flash microcontroller having part number PIC16F1824 that is available from Microchip Technology Inc. of Mission Viejo, Calif. The microcontroller 30 is accompanied by suitable support circuitry, including a battery connected to the plus (+) and minus (−) terminals in FIG. 5. It is programmed in line with known techniques to function as herein described. A USB port 40 (FIG. 4) facilitates communication with the microcontroller 30.

Preferably, the tone-producing circuitry 20 of the electrolarynx 10 is configured to enable the user to set a user-selected one of multiple sensitivity levels for the FVM and VVM operational modes of the electrolarynx 10. In other words, the tone-producing circuitry 20 is configured to respond to variations in PSR resistance with a degree of sensitivity to PSR resistance that the user sets with the mode switch. Depressing the mode button once (1) after initially powering up the electrolarynx 20, for example, results in the first FVM at a first or low FVM sensitivity level (i.e., changes in frequency are relatively less sensitive to variations in PSR resistance). Similarly, depressing the mode button twice (2) results in a second FVM at a second or low-medium FVM sensitivity level, depressing it three (3) times results in a third FVM at a third or high-medium FVM sensitivity level, and depressing it four (4) times results in a fourth FVM at a fourth or high FVM sensitivity level.

For multiple volume-varying modes, depressing the mode button five (5) times results in the first VVM at a first or low VVM sensitivity level, and depressing the mode button six (6) times results in a second VVM at a second or high VVM sensitivity level. After that, depressing the mode button seven (7) times results in the communications-link mode of electrolarynx operation (i.e., control by an extern al device via the communications link), and depressing the mode button eight (8) times results in the disabled mode (i.e., the other modes of electrolarynx operation are disabled). For additional depressions of the mode switch, the tone-producing circuitry 20 recycles though the operational modes described above for the mode-switch depressions one through eight, doing it that way until the next initial power-up of the electrolarynx (e.g., battery change), at which time it begins anew as described above for the first mode-switch depression after initial power-on.

To summarize the nomenclature used herein for the various frequency-varying and volume-varying modes:

1. The first frequency-varying mode is a first VVM in which the tone-producing circuitry varies the frequency of the electrolarynx tone according to variations in the resistance value of the pressure-sensitive resistor, doing so at a first FVM sensitivity to the resistance value of the pressure-sensitive resistor (e.g., a low FVM sensitivity level).
2. The second frequency-varying mode is a second VVM in which the tone-producing circuitry varies the frequency of the electrolarynx tone according to variations in the resistance value of the pressure-sensitive resistor, doing so at a second FVM sensitivity to the resistance value of the pressure-sensitive resistor (e.g., a low-medium FVM sensitivity level).
3. The third frequency-varying mode is a third VVM in which the tone-producing circuitry varies the frequency of the electrolarynx tone according to variations in the resistance value of the pressure-sensitive resistor, doing so at a third FVM sensitivity to the resistance value of the pressure-sensitive resistor (e.g., a high-medium FVM sensitivity level).
5. The fourth frequency-varying mode is a fourth VVM in which the tone-producing circuitry varies the frequency of the electrolarynx tone according to variations in the resistance value of the pressure-sensitive resistor, doing so at a fourth FVM sensitivity to the resistance value of the pressure-sensitive resistor (e.g., a high FVM sensitivity level).
6. The first volume-varying mode is a first VVM in which the tone-producing circuitry varies the volume of the electrolarynx tone according to variations in the resistance value of the pressure-sensitive resistor, doing so at a first volume-varying-mode (VVM) sensitivity to the resistance value of the pressure-sensitive resistor (e.g., a low VVM sensitivity level).
7. The second volume-varying mode is a second VVM in which the tone-producing circuitry varies the volume of the electrolarynx tone according to variations in the resistance value of the pressure-sensitive resistor, doing so at a second VVM sensitivity to the resistance value of the pressure-sensitive resistor (e.g., a high VVM sensitivity level).

Concerning the communications-link mode of electrolarynx operation, the electrolarynx 10 includes communication circuitry 50 for that purpose (FIG. 4). It communicates, for example, with an external device (not shown) that is not physically connected to the electrolarynx 10. The communication circuitry 50 is connected to the tone-producing circuitry 20 and may use known technology, including, for example, 2.45 GHz radio frequency (RF) communications and/or an infrared (IR) receiver. Frequency and/or volume information is communicated from the external device via the circuitry 50.

From the descriptions provided and those incorporated by reference, a person having ordinary skill in the art can readily provide suitable circuitry for the communication link. Any of various transmission, reception, and encoding methods may be used, including wire, radio, and infrared. The illustrated communications circuitry 50 may include, for example, an infrared sensor (not shown) that extends through an opening in the case 11 where it receives an infrared signal on which at least one of on-off information, frequency information, and volume information is encoded. That information is encoded at the external device, for example, in response to a pressure sensor placed proximate an opening in the user's throat through which the user exhales (e.g., a surgical opening called a stoma).

Thus, the invention provides an electrolarynx having a pushbutton for turning on the electrolarynx tone, a PSR coupled to the pushbutton, tone-producing circuitry for producing variations in attributes of the electrolarynx tone according to variations in the resistance of the PSR, and a mode switch for enabling a user to select the tone attributes affected. Although an exemplary embodiment has been shown and described, one of ordinary skill in the art may make many changes, modifications, and substitutions without necessarily departing from the spirit and scope of the invention. The specific terminology used to describe the exemplary embodiment is not intended to limit the inven-

What is claimed is:

1. An electrolarynx, comprising:
    a case;
    tone-producing circuitry on the case for producing an electrolarynx tone having a frequency and a volume;
    a power switch on the case for turning on power to the tone-producing circuitry;
    a pushbutton on the case for enabling a user to activate the power switch;
    a pressure-sensitive-resistor on the case that is physically coupled to the pushbutton so that the pressure-sensitive resistor has a resistance value dependent on pressure applied by the user to the pushbutton; and
    a mode switch on the case that is electrically connected to the tone-producing circuitry;
    wherein the tone-producing circuitry is configured to operate in a first frequency-varying mode in which the tone-producing circuitry varies the frequency of the electrolarynx tone according to variations in the resistance value of the pressure-sensitive resistor, doing so at a first frequency-varying mode sensitivity to the resistance value of the pressure-sensitive resistor;
    wherein the tone-producing circuitry is configured to operate in a first volume-varying mode in which the tone-producing circuitry varies the volume of the electrolarynx tone according to variations in the resistance value of the pressure-sensitive resistor, doing so at a first volume-varying mode sensitivity to the resistance value of the pressure-sensitive resistor; and
    wherein the tone-producing circuitry is configured to enable a user to select a desired mode of electrolarynx operation by operation of the mode switch.

2. An electrolarynx, as recited in claim 1, wherein:
    the electrolarynx includes communications circuitry for providing a communications link with a device that is not physically connected to the electrolarynx;
    the tone-producing circuitry is configured to operate in a communications-link mode in which the tone-producing circuitry responds to control information received via the communications link; and
    wherein the tone-producing circuitry is configured to enable a user to select the communications-link mode by operation of the mode switch.

3. An electrolarynx, as recited in claim 1, wherein:
    the tone-producing circuitry is configured to operate in a disabled mode in which the frequency-varying mode, the volume-varying mode, and the communications-link mode are disabled; and
    wherein the tone-producing circuitry is configured to enable a user to select the disabled mode by operation of the mode switch.

4. An electrolarynx, as recited in claim 1, wherein:
    the tone-producing circuitry is configured to operate in multiple modes of electrolarynx operation; and
    the tone-producing circuitry is configured to respond to a predetermined number of mode switch closures in setting a corresponding user-selected mode of electrolarynx operation.

5. An electrolarynx, as recited in claim 1, wherein the tone-producing circuitry is configured to operate in multiple frequency-varying modes such that each of said multiple frequency-varying modes has a different frequency-varying mode sensitivity to the resistance value of the pressure-sensitive resistor; and the tone-producing circuitry is configured to operate in a user-selected one of said multiple frequency-varying modes according to operation of the mode switch.

6. An electrolarynx, as recited in claim 1, wherein the tone-producing circuitry is configured to operate in multiple volume-varying modes such that each of said multiple volume-varying modes has a different volume-varying mode sensitivity to the resistance value of the pressure-sensitive resistor; and the tone-producing circuitry is configured to operate in a user-selected one of said multiple volume-varying modes according to operation of the mode switch.

7. An electrolarynx, as recited in claim 1, wherein the tone-producing circuitry is configured to operate in multiple modes of electrolarynx operation according to operation of the mode switch so that (1) a first closure of the mode switch sets the first frequency-varying mode at the first frequency-varying mode sensitivity, (2) a second closure of the mode switch sets a second frequency-varying mode at a second frequency-varying mode sensitivity, (3) a third closure of the mode switch sets a third frequency-varying mode at a third frequency-varying mode sensitivity, (4) a fourth closure of the mode switch sets a fourth frequency-varying mode at a fourth frequency-varying mode sensitivity, (5) a fifth closure of the mode switch sets the first volume-varying mode at the first volume-varying mode sensitivity (6) a sixth closure of the mode switch sets a second volume-varying mode at a second volume-varying mode sensitivity, (7) a seventh closure of the mode switch sets the communications-link mode, and (8) an eighth closure of the mode switch sets the disabled mode.

* * * * *